United States Patent
Cao et al.

(10) Patent No.: US 9,801,595 B2
(45) Date of Patent: Oct. 31, 2017

(54) COUNT-WEIGHTED LEAST SQUARES PARAMETER ESTIMATION FOR A PHOTON-COUNTING DETECTOR

(71) Applicant: Toshiba Medical Systems Corporation, Otawara-shi (JP)

(72) Inventors: Chunguang Cao, Buffalo Grove, IL (US); Xiaolan Wang, Buffalo Grove, IL (US); Yu Zou, Naperville, IL (US)

(73) Assignee: Toshiba Medical Systems Corporation, Otawara-shi (JP)

( * ) Notice: Subject to any disclaimer, the term of this patent is extended or adjusted under 35 U.S.C. 154(b) by 569 days.

(21) Appl. No.: 14/479,955

(22) Filed: Sep. 8, 2014

(65) Prior Publication Data

US 2016/0070008 A1 Mar. 10, 2016

(51) Int. Cl.
| | |
|---|---|
| *A61B 6/03* | (2006.01) |
| *A61B 6/00* | (2006.01) |
| *G01T 1/36* | (2006.01) |
| *G01T 1/17* | (2006.01) |
| *G01T 1/24* | (2006.01) |

(52) U.S. Cl.
CPC ............ *A61B 6/4241* (2013.01); *A61B 6/032* (2013.01); *A61B 6/482* (2013.01); *A61B 6/5205* (2013.01); *A61B 6/585* (2013.01); *G01T 1/17* (2013.01); *G01T 1/247* (2013.01); *G01T 1/36* (2013.01)

(58) Field of Classification Search
CPC ....... A61B 6/032; A61B 6/4241; A61B 6/482; A61B 6/5205; G01T 1/36
See application file for complete search history.

(56) References Cited

U.S. PATENT DOCUMENTS

| | | | | | |
|---|---|---|---|---|---|
| 5,692,507 | A | * | 12/1997 | Seppi | A61B 6/032 128/920 |
| 6,895,077 | B2 | * | 5/2005 | Karellas | A61B 6/481 250/370.09 |
| 8,886,284 | B2 | * | 11/2014 | Pogue | A61B 5/0091 600/411 |
| 2003/0169847 | A1 | * | 9/2003 | Karellas | A61B 6/481 378/98.3 |
| 2007/0206721 | A1 | * | 9/2007 | Tkaczyk | A61B 6/032 378/19 |
| 2008/0071164 | A1 | * | 3/2008 | Pogue | A61B 5/0091 600/411 |

(Continued)

*Primary Examiner* — Thomas R Artman
(74) *Attorney, Agent, or Firm* — Oblon, McClelland, Maier & Neustadt, L.L.P.

(57) ABSTRACT

A method and apparatus for estimating a parameter vector including a plurality of parameters of a detector response model of a photon-counting detector. The method includes calculating a modeled spectrum based on an input spectrum and an initial value of the plurality of parameters. For each detector, a difference between the normalized photon count of the measured spectrum and the normalized modeled spectrum is calculated. A root mean square error (RMSE) between the measured and modeled spectra is obtained by squaring the normalized difference and weighting the normalized difference by a weighting factor. The parameter vector is updated until an optimum RMSE value is achieved. Upon determining optimal values of the parameter vector, measured data that is obtained via a patient scan is corrected based on the optimal parameter vector.

20 Claims, 5 Drawing Sheets

(56) References Cited

U.S. PATENT DOCUMENTS

| | | | |
|---|---|---|---|
| 2008/0135789 A1* | 6/2008 | Du | A61B 6/032 250/580 |
| 2009/0039273 A1* | 2/2009 | Tkaczyk | G01T 1/171 250/370.06 |
| 2015/0122992 A1* | 5/2015 | Owen | G01N 23/225 250/307 |
| 2016/0070008 A1* | 3/2016 | Cao | A61B 6/4241 378/5 |

* cited by examiner

COUNT-WEIGHTED LEAST SQUARES PARAMETER ESTIMATION FOR A PHOTON-COUNTING DETECTOR

FIELD

Embodiments disclosed herein generally relate to computed tomography (CT) imaging. In particular, embodiments disclosed herein relate to a CT apparatus including a plurality of photon-counting detectors and an associated method thereof for estimating parameters of a response function of the photon-counting detectors.

BACKGROUND

CT systems and methods are widely used, particularly for medical imaging and diagnosis. In CT systems, an X-ray beam traverses an object and a detector relates the overall attenuation per ray. The attenuation is derived from a comparison of the same ray with and without the presence of the object. From this conceptual definition, several steps are required to properly construct an image. For instance, the finite size of the X-ray generator, the nature and shape of the filter blocking the very low energy X-ray from the generator, the details of the geometry and characteristics of the detector, and the capacity of the acquisition system are all elements that affect how the actual reconstruction is performed.

Many clinical applications can benefit from spectral CT technology, which can provide improvement in material differentiation and beam hardening correction. Further, semiconductor-based photon-counting detectors are a promising candidate for spectral CT, which is capable of providing better spectral information compared with conventional spectral CT technology (e.g., dual-source, kVp-switching, etc.).

Photon-counting detectors are configured to acquire the spectral nature of the X-ray source. To obtain the spectral nature of the transmitted X-ray data, the photon-counting detector counts a number of photons in each of a plurality of energy bins. The use of the spectral nature of the X-ray source in CT is often referred to as spectral CT. Since spectral CT involves the detection of transmitted X-rays at two or more energy levels, spectral CT generally includes dual-energy CT by definition.

Semiconductor based photon-counting detectors used in spectral CT can detect incident photons and measure photon energy for every event. However, due to factors such as interaction depth and ballistic deficit, the measured photon energy cannot be related to incident photon energy uniquely. Furthermore, at high flux, pulse-pileup may also cause a loss in photon count. Accordingly, accurate image reconstruction can be achieved by efficiently estimating parameters of a response function of the photon-counting detectors.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1:
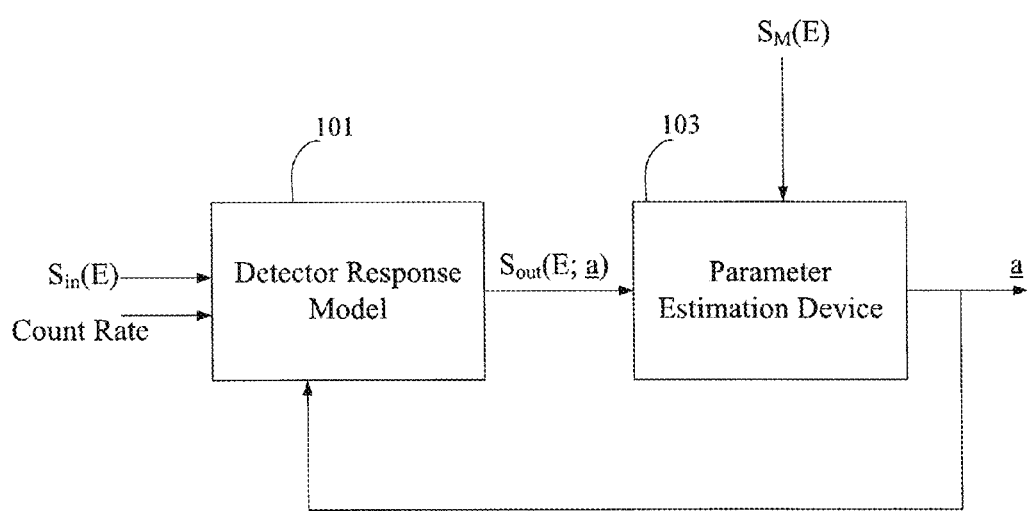
FIG. 1 illustrates an apparatus for determining parameters of a response function for a photon-counting detector.

Embodiments described herein are directed to a CT apparatus including a plurality of photon-counting detectors and a method for estimating parameters of a response function of the photon-counting detectors.

Different types of artifacts may corrupt a reconstructed X-ray image. Some artifacts are caused by an object itself. For example, the motion artifact that occurs when the object moves during an acquisition time period, a metal artifact that results due to the object having metallic dental fillings or implants, and an artifact that results from an X-ray source that emits X-rays of multiple energies, known as the beam-hardening artifact. Furthermore, the photon-counting detector's response may vary with the X-ray's incident angle. This phenomenon is referred to as the polar effect. The polar effect usually occurs at a non-normal entrance of incident rays of photons and results in ambiguity in determining the response of the photon counting detector and thus degrades the overall spatial resolution in medical image systems.

Accordingly, an accurate detector response function for semiconductor-based X-ray photon-counting detectors is required to accurately reconstruct an image. The detector's response function may model a weighting potential that describes how electrons/holes form and induce an electrical signal in the semiconductor, a ballistic deficiency that corresponds to a detector's failure of capturing an entire signal, a polar effect caused by relative orientation of the source and detector, a K-escape phenomenon that defines the amount of energy of the incident spectrum that escapes from the detector, inter-pixel crosstalk, a space charge phenomenon wherein an electric field reduces a migration rate of electrons/holes, etc. A parameter vector that includes a plurality of parameters can model the above-described detector characteristics.

Therefore, the parameters that define the response function of the photon-counting detector need to be estimated correctly in order to correct physical effects in the measured data that are used in material decomposition and reconstruction of spectral CT images.

According to one embodiment, there is provided a method for determining a parameter vector that includes a plurality of parameters of a detector response model of a photon-counting detector, the method including: normalizing a measured photon count for each energy bin of the photon-counting detector; setting an initial value of an incident photon spectrum and each parameter of the plurality of parameters; calculating and normalizing, a modeled photon count for each energy bin of the photon-counting detector based on the incident photon spectrum and the plurality of parameters; computing for each energy bin, a square of a difference between the normalized measured photon count and the normalized modeled photon count; weighting the computed square of each energy bin by a weighting factor; summing the weighted squares of each energy bin and computing a root mean square error of the photon counting detector; updating at least one of the values of the parameter vector; and repeating the calculating and normalizing, computing, weighting, summing, and updating steps until a stopping criteria is met, so as to determine the parameter vector that optimizes the root mean square error.

According to another embodiment is provided a computed-tomography (CT) apparatus for determining a parameter vector that includes a plurality of parameters of a detector response model of a photon-counting detector, the CT apparatus includes a rotating X-ray source configured to emit X-rays; a stationary photon-counting detector configured to receive X-rays emitted from the X-ray source; and a processing circuit that is configured to: normalize a measured photon count for each energy bin of the photon-counting detector; set an initial value of an incident photon spectrum and each parameter of the plurality of parameters; calculate and normalize, a modeled photon count for each energy bin of the photon-counting detector based on the incident photon spectrum and the plurality of parameters; compute for each energy bin, a square of a difference between the normalized measured photon count and the normalized modeled photon count; weight the computed square of each energy bin by a weighting factor; sum the weighted squares of each energy bin and compute a root mean square error of the photon counting detector; update at least one of the values of the parameter vector; and repeat the calculating and normalizing, computing, weighting, summing and updating steps until a stopping criteria is met, so as to determine the parameter vector that optimizes the root mean square error.

In another embodiment, there is provided a non-transitory computer readable medium having stored thereon a program that when executed by a computer, causes the computer to execute a method, the method includes the steps of: normalizing a measured photon count for each energy bin of the photon-counting detector; setting an initial value of an incident photon spectrum and each parameter of the plurality of parameters; calculating and normalizing, a modeled photon count for each energy bin of the photon-counting detector based on the incident photon spectrum and the plurality of parameters; computing for each energy bin, a square of a difference between the normalized measured photon count and the normalized modeled photon count; weighting the computed square of each energy bin by a weighting factor to generate weighted squares; summing the weighted squares of each energy bin and computing a root mean square error of the photon counting detector; updating at least one of the values of the parameter vector; and repeating the calculating and normalizing, computing, weighting, summing and updating steps until a stopping criteria is met, so as to determine the parameter vector that optimizes the root mean square error.

Turning now to the drawings, FIG. 1 illustrates an apparatus for determining parameters of a response function for each photon-counting detector in a spectral CT scanner. In particular, FIG. 1 illustrates a detector response model 101 that receives an incident spectrum $S_{in}(E)$, a count rate, and a parameter vector a. Based on the received values, the detector response model 101 generates a modeled spectrum $S_{out}(E; a)$. For instance, the modeled spectrum may be generated by sequentially computing a first component spectrum $S_0(E)$ from single-photon events according to Poisson distribution, a second component spectrum $S_1(E)$ from double-photon events according to Poisson distribution and $S_{in}(E)$, and a third component spectrum $S_2(E)$ from multiple (more than two) photon events according to Poisson distribution and $S_{in}(E)$. The modeled spectra may be computed as a sum of the first, second, and third component spectra, respectively.

As shown in FIG. 1, the model parameter estimation device 103 compares the modeled spectrum $S_{out}(E; a)$ with an actual measured spectrum $S_M(E)$, and updates the parameter vector a so as to minimize a predetermined criteria. Specific details regarding the minimization of the criteria will be described in more detail below. The updated parameter vector a is fed back to the detector response model to generate a new modeled spectrum $S_{out}(E; a)$. According to one embodiment, this process continues until the predetermined criterion is achieved. Alternatively, the process continues for a predetermined number of iterations or until the change in the parameter vector a falls below a predetermined threshold. As described below, the model parameter estimation device can employ, e.g., an exhaustive search within a predefined range for the parameter vector a, or a nonlinear least-squares method for finding the optimal parameter vector a. A respective optimal parameter a is found for each photon-counting detector in the scanner.

The input spectrum $S_{in}(E)$ can be determined by calculation (all vendors have models to calculate the output from their tubes) or measurements (by using a gold-standard spectroscopic detector, e.g., a high-purity germanium spectrometer) for each photon-counting detector (PCD) in a scanner. The measured spectrum $S_M$ is the output spectrum from each PCD corresponding to each incident spectrum.

The parameter vector a can include parameters for a weighting potential that describes how electrons/holes form and induce an electrical signal in the semiconductor, a ballistic deficiency that corresponds to a detectors failure of capturing an entire signal, a polar effect caused by relative orientation of the source and detector, a K-escape phenomenon that defines the amount of energy of the incident spectrum that escapes from the detector, inter-pixel crosstalk, a space charge phenomenon wherein an electric field reduces the rate migration of electrons/holes and the like.

As noted above, the model parameter estimation device 103 shown in FIG. 1 compares the modeled spectrum $S_{out}(E; a)$ with an actual measured spectrum $S_M(E)$, and updates the parameter vector a so as to minimize a predetermined criteria. The method used to find the optimal parameter values a is shown in FIG. 2.

Figure 2:
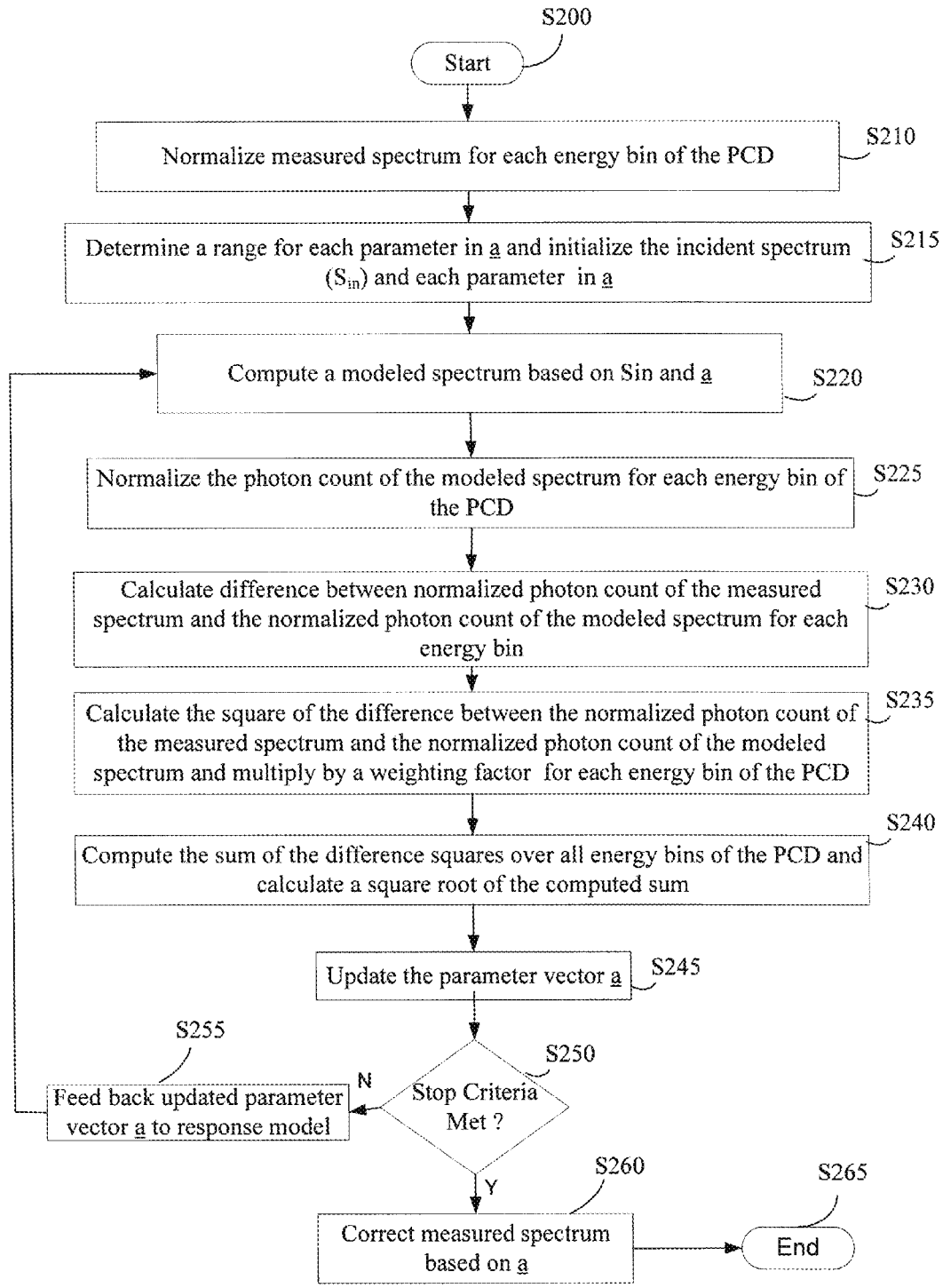
FIG. 2 illustrates a method performed by a parameter estimation device.

FIG. 2 illustrates a method performed by a parameter estimation device. Each detector includes a total of N energy bins. The measured photon count for each energy bin is represented as $C_k$, wherein k is an index for a particular bin included in each PCD. Specifically, k varies from 1, 2, 3, . . . N. The measured spectrum for the detector is represented as $C_{TOT}$, and can be computed as follows:

$$C_{TOT} = \sum_{k=1}^{k=N} C_k \qquad (1)$$

The method performed by the parameter estimation device begins in step S200 and proceeds to step S210. In step S210, the measured spectrum for each detector bin of the PCD is normalized with respect to the total measured spectrum. Specifically, the normalized measured spectrum $\overline{C_k}$, for each energy bin of the PCD can be calculated as follows:

$$\overline{C_k} = \frac{C_k}{C_{TOT}} \qquad (2)$$

In step S215, suitable ranges for each of the parameters in the parameter vector a are defined. Specifically, the range of each parameter is determined by the detector's electronic properties as well as the physical operation of the detector's sensor. For instance, consider a detector model that includes six parameters: peaking time, dead time, DAC to keV gain, DAC to keV offset, Gaussian smooth standard deviation, and peak pileup and tail pileup thresholds. In this case, the peaking time, dead time and peak-tail pileup threshold parameters are determined by detector electronics, whereas the parameters DAC to keV gain, DAC to keV offset, and Gaussian smooth standard deviation are determined by both electronics and sensor physics.

According to one example, the parameter peaking time is based on a user's input and electrical circuit properties. For example, if the user sets the peaking time to be around 40 ns, then the range to search for the best peaking time for the response model can be set to be 10 to 80 ns. Further, the parameter dead time is approximately twice the magnitude of the peaking time. Therefore, the range to search for the best dead time can be set to be 20 to 100 ns, for example. Additionally, the parameter DAC to keV gain is typically around 0.1 to 0.2. Therefore, the search range for DAC to keV gain can be set to 0.1 to 0.3, for example. The parameter DAC to keV offset must be a positive number and is not very large. Therefore, the search range of DAC to keV offset can be set to 0 to 25, for example. The parameter Gaussian smooth standard deviation is around 2.7. Thus, the search range for the Gaussian smooth standard deviation parameter can be set to 1 to 6, for example. The peak pileup and tail pileup thresholds must lie in the range from zero to the dead time. Therefore, the search range for peak pileup and tail pileup can be set, for example, to 0 to 100 ns. Further, as shown in step S215, the input spectrum $S_{in}(E)$ and each parameter of the parameter vector a are initialized to an initial value.

In step S220, a modeled spectrum is computed for each energy bin ($S_{out}(E; a)_k$) of the PCD based on the input spectrum $S_{in}(E)$ and the parameter vector a.

The process then moves to step S225, wherein the photon count of the computed modeled spectrum for each energy bin is normalized with respect to the total photon count of the modeled spectrum of the PCD. Specifically, the normalized form of the photon count of the simulated measured spectrum for each energy bin $\overline{S_{out}(a)_k}$, can be computed as follows:

$$\overline{S_{out}(\underline{a})_k} = \frac{S_{out}(\underline{a})_k}{S_{out}(\underline{a})} \quad (3)$$

wherein $$S_{out}(\underline{a})_k = \int_{T_{k\_low}}^{T_{k\_high}} S_{out}(E; \underline{a})dE,$$

$$S_{out}(\underline{a}) = \sum_{k=1}^{k=N} S_{out}(\underline{a})_k,$$

where $T_{k\_low}$ and $T_{k\_high}$ are the low and high energy thresholds that define the $k^{th}$ energy bin, and $S_{out}(a)$ is the total photon count of the modeled spectrum for the PCD.

In step S230, a difference between the normalized photon count of the measured spectrum and the normalized photon count of the modeled spectrum is computed for each detector bin. The difference between the photon counts for energy bin k ($\overline{\Delta_k}$) can be represented as:

$$\overline{\Delta_k} = \overline{C_k} - \overline{S_{out}(a)_k} \quad (4)$$

In step S235, a square of the computed difference between the normalized photon count of the measured spectrum and the normalized photon count of the modeled spectrum (of step S230) is computed. The computed square for each energy bin of the PCD is further weighted by a weighing factor ($\Phi_k$). According to one embodiment, the weighting factor is the normalized photon count of the measured spectrum of the particular energy bin. Thus, the weighted square of a particular energy bin k, can be represented as:

$$\overline{\Delta_k}^2 = \Phi_k (\overline{C_k} - \overline{S_{out}(a)_k})^2 \quad (5)$$

wherein $\Phi_k = \overline{C_k}$. Thus, as shown in equation (5), a least squares formulation is obtained for each energy bin, wherein the weight associated with each bin corresponds to normalized photon count of the measured spectrum. Thus, the least squares computation according to the present embodiment puts more emphasis on energy bins with a high data count by weighting the difference between the normalized photon count of the measured spectrum and the normalized photon count of the modeled spectrum of the energy bin, with its corresponding normalized measured spectrum.

In step S240, a sum of the difference squares for each energy bin is calculated. Further, a square root of the sum is calculated to obtain a root mean square error (RMSE). Specifically, the RMSE of the photon counting detector can be computed as follows:

$$\text{RMSE} = \sqrt{\sum_{k=1}^{k=N} \varphi_k (\overline{C_k} - \overline{S_{out}(\underline{a})_k})^2},$$

wherein $\overline{C_k}$ is the normalized measured spectrum of detector bin k, $\overline{S_{out}(a)_k}$ is the normalized modeled spectrum of the detector bin k, $\Phi_k$ is the weighting factor for detector bin k, and N is the number of detector bins in the photon-counting detector.

In step S245, the parameter vector a is updated based on the particular optimization method used. For example, if an exhaustive search algorithm is being used, the vector a is updated in a predetermined systematic manner within the range defined for each parameter. Alternatively, a nonlinear least-squares fitting method, such as Levenberg-Marquardt, can be used. According to one embodiment, a simple global search of the parameter vector a can be implemented in such a manner that the parameter vector of interest is one that has the minimum amount of RMSE. In order to find the values of the parameters in the parameter vector a that achieve the minimum RMSE, the parameters can be updated in order by looping through all possible combinations of the parameters.

According to other embodiments, the parameters can be updated according to Newton's method, steepest descent, non-linear conjugate gradient method, etc. Furthermore, the RMSE can also be computed based on the absolute photon count of the measured and modeled spectra.

The process further moves to step S250 wherein a query is made to check if a stopping criteria is satisfied. If the response to the query is affirmative, the process proceeds to step S260. If the response to the query is negative, the process moves to step S255. The stopping criteria, according to an embodiment may be a query to check if the smallest RMSE is achieved. According to another embodiment, the stopping criteria may be a query to determine if a predetermined number of iterations have been performed to update the parameter vector a.

Upon the query in step S250 being negative, the process moves to step S255 wherein the updated parameter vector a is fed back to the detector response model. Specifically, the process loops back to step S220, wherein a new modeled spectrum $S_{out}(a)$ using the updated parameter vector a is computed.

If the response to the query of step S250 was affirmative, the process moves to step S260 wherein the measured spectrum data that is obtained, for example, from patient CT scans, is corrected based on the optimal parameter vector a. For instance, with an updated parameter vector, the pileup component can be calculated and thereafter subtracted from the measured spectrum to correct the measured spectrum that is obtained from the CT scan. A detailed description of the technique of using the updated parameter vector to correct the measured spectrum is provided in U.S. patent application Ser. No. 13/866,965, which is incorporated herein by reference in its entirety. After correcting the measured spectrum data, the process ends in step S265.

Figure 3A:
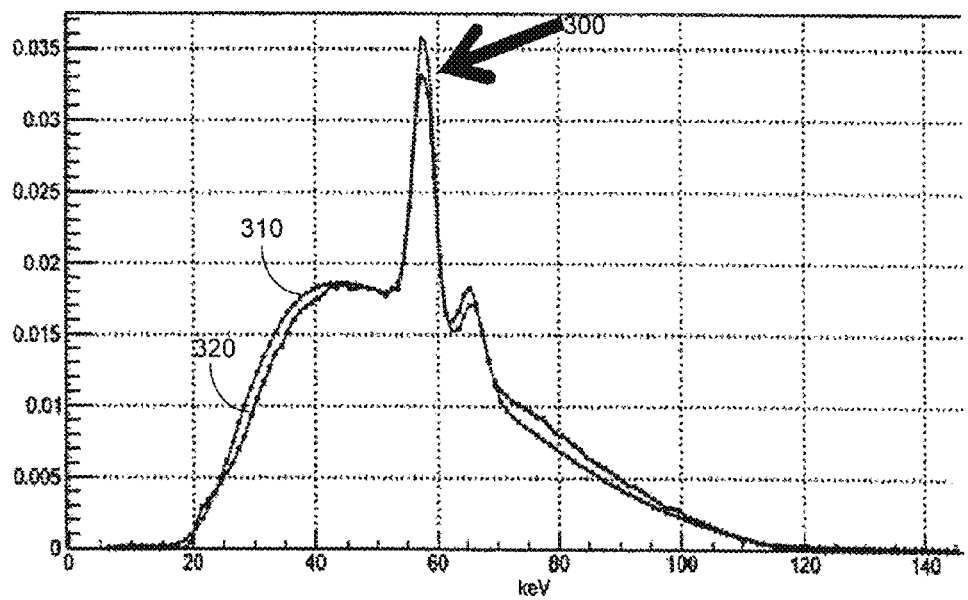
FIGS. 3A and 3B show a graph illustrating a comparison of a modeled spectrum with a measured spectrum according to one embodiment.
Figure 3B:
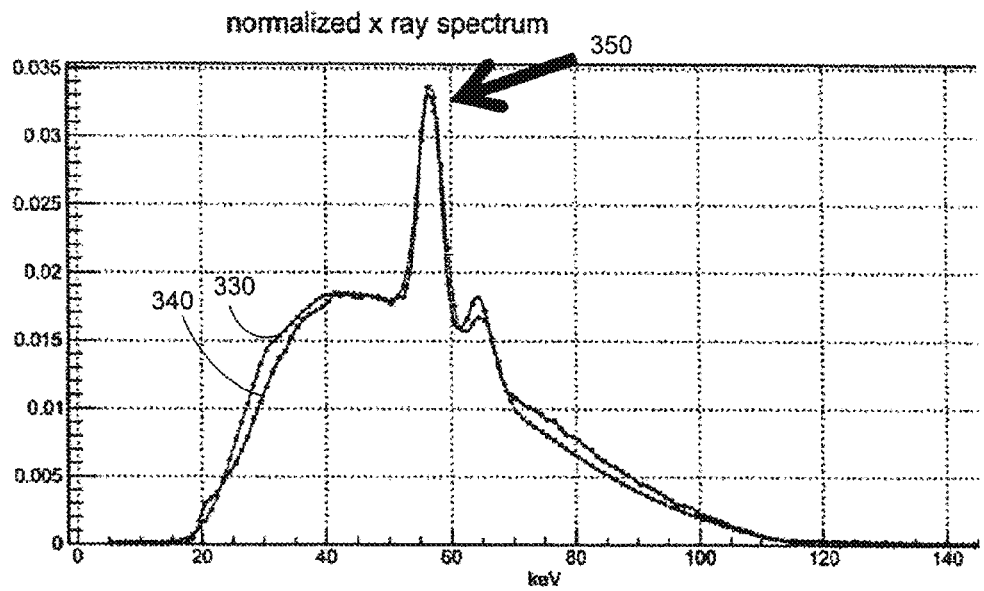

FIGS. 3A and 3B show a graph illustrating a comparison of a modeled spectrum to a measured spectrum according to one embodiment. FIG. 3A depicts two curves: curve 310, which corresponds to a normalized measured X-ray spectrum and curve 320, which corresponds to a modeled X-ray spectrum. The data corresponding to curve 310 is obtained from a single isolated detector element at low flux.

FIG. 3A depicts the modeled and measured X-ray spectrums that are computed without using a weighting factor in the RMSE calculation. When weighting factors are not used in the RMSE calculation, there is a mismatch at a peak point 300 between the measured spectrum and the modeled spectrum.

In contrast, FIG. 3B depicts two curves: curve 330, which corresponds to a normalized measured X-ray spectrum, and curve 340, which corresponds to a modeled X-ray spectrum. In FIG. 3B, the curves 330 and 340 are obtained by using a weighting factor in the RMSE calculation as described above with reference to FIG. 2. When a weighting factor that corresponds to the normalized photon count of the measured spectrum, a better matching of the curves 330 and 340 is obtained at a peak point 350. Accordingly, the use of weighting factors in the RMSE calculation improves the accuracy of the detector response parameter estimation.

Figure 4:
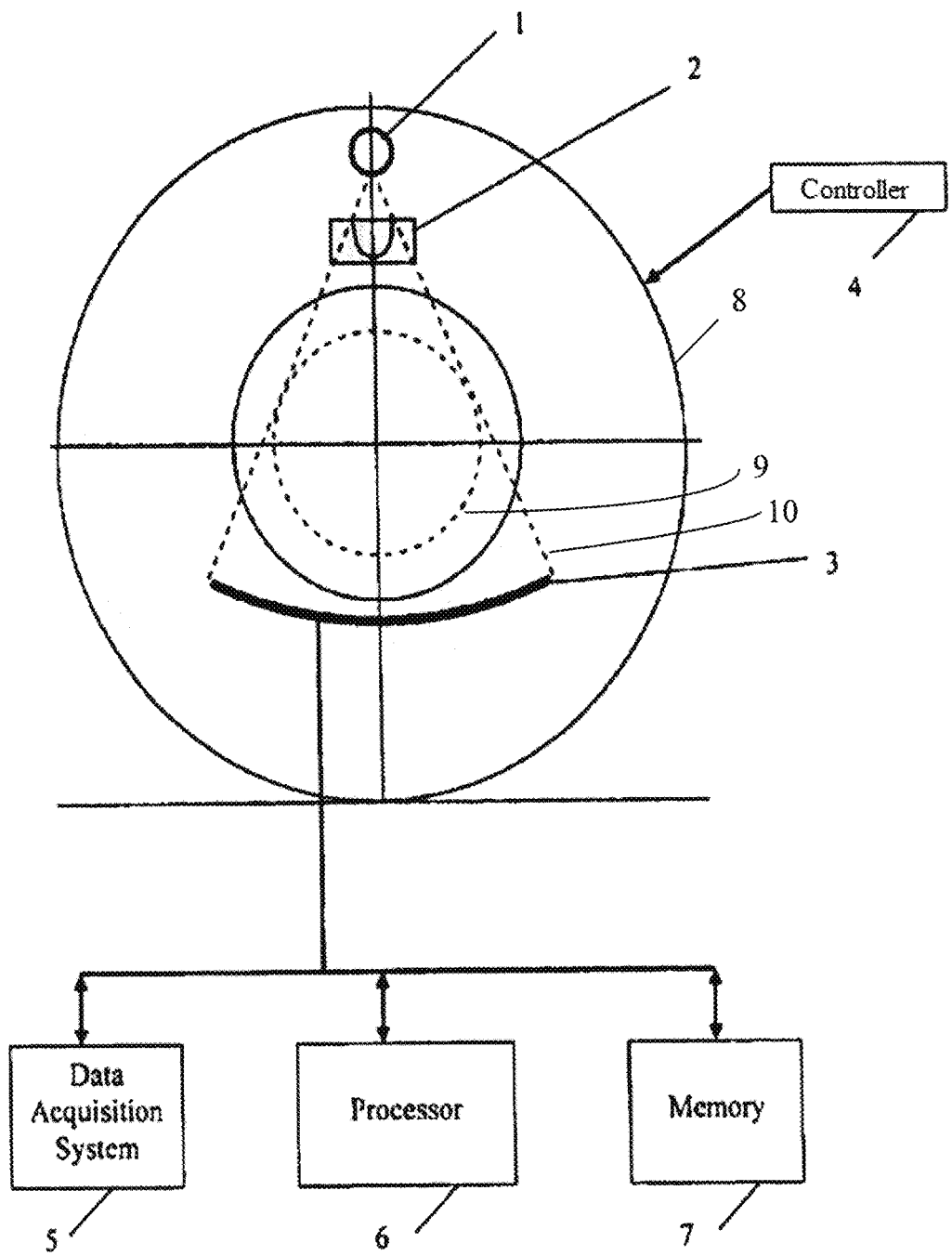
FIGS. 4 and 5 illustrate a CT scanner system according to the present embodiments.
Figure 5:
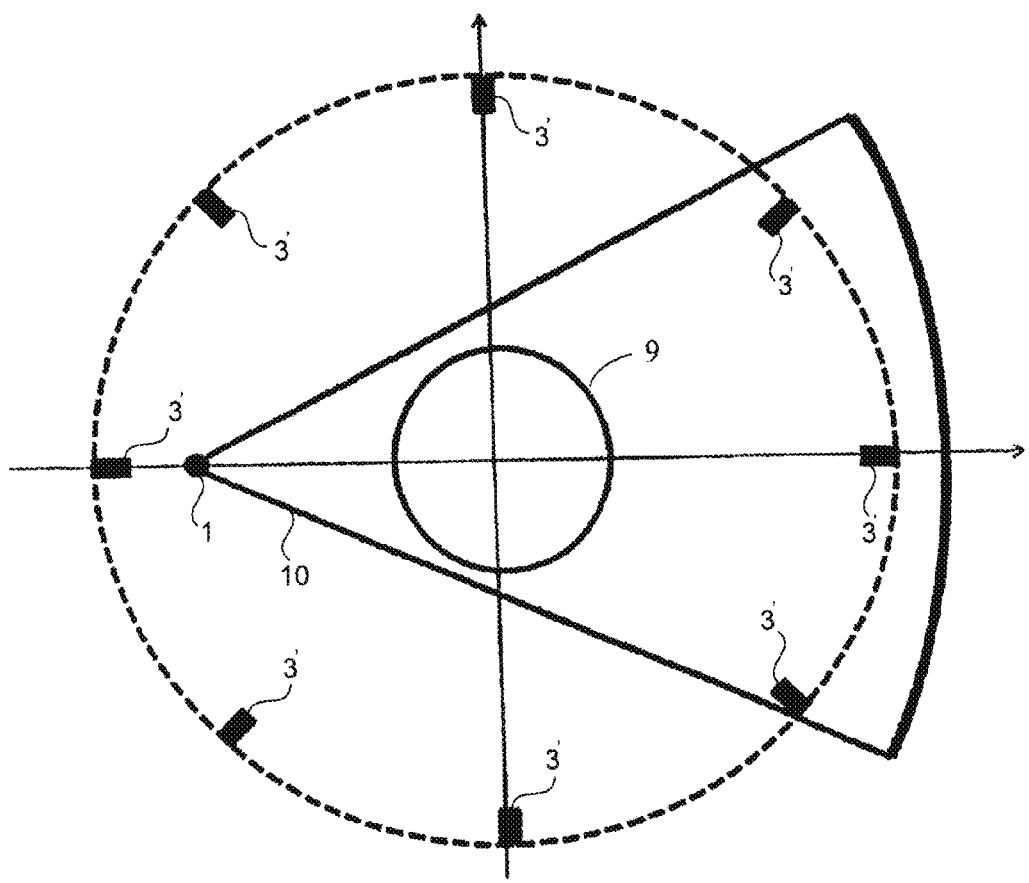

FIG. 4 illustrates the basic structure of a spectral CT scanner apparatus that includes the photon-counting detectors described herein. The CT apparatus of FIG. 4 includes an X-ray tube 1, filters and collimators 2, and detector 3. The CT apparatus may also include, for example, sparse fixed energy-discriminating (e.g., photon-counting) detectors 3', which can be arranged at a different radius from that of the third-generation detector, as shown in FIG. 5. The CT apparatus will also include additional mechanical and electrical components, such as a gantry motor and a controller 4 to control the rotation of the gantry, control the X-ray source, and control a patient bed. The CT apparatus also includes a data acquisition system 5 and a processor 6 to generate CT images based on the projection (view) data acquired by the data acquisition system. For example, the processor 6 included a reconstruction processor to reconstruct spectral CT images.

The X-ray tube 1, filters and collimators 2, detector 3, and controller 4 can be provided in a frame 8 that includes a bore. The frame 8 has a general cylindrical or donut shape.

In the view shown in FIG. 4, a longitudinal axis of the bore of the frame 8 is in the center of the bore and extends into and out of the page. An interior of the bore, identified as area 9, is a target area for imaging. An object to be scanned, such as a patient, is placed in the target area with, e.g., a patient table. The object can then be irradiated by the X-ray tube 1 with a fan or cone of radiation 10, which generally, substantially or effectively cross-sects the object with respect to the longitudinal axis.

The processor 6 is programmed to perform methods for determining parameters of a detector response model and for performing correction of measured data for each photon-counting detector. Further, the processor and data acquisition system make use of a memory 7, which is configured to store, e.g., computer programs, data obtained from the detector, the detector response model parameters, and reconstructed images.

In one embodiment, the processor is configured to normalize a measured photon count for each energy bin of the photon-counting detector and determine a range for each parameter of the plurality of parameters and set an initial value of an incident photon spectrum and each parameter of the plurality of parameters. Further, the processor is configured to calculate and normalize, a modeled photon count for each energy bin of the photon-counting detector based on the incident photon spectrum and the plurality of parameters. The processor also computes for each energy bin, a square of a difference between the normalized measured photon count and the normalized modeled photon count and weights the computed square of each energy bin by a weighting factor.

The processor computes the sum of the weighted squares of each energy bin and computes a root mean square error of the photon counting detector. Upon computing the root mean square error, the processor updates at least one of the values of the parameter vector, and repeats the calculating and normalizing, computing, weighting, summing and updating steps until a stopping criterion is met, so as to determine the parameter vector that optimizes the root mean square error.

As one of ordinary skill in the art would recognize, the processor 6 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the reconstruction processor may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art.

Once processed by the pre-reconstruction processor, the processed signals are passed to the reconstruction processor, which is configured to generate CT images. The images are stored in the memory, and/or displayed on a display. As one of ordinary skill in the art would recognize, memory can be a hard disk drive, CD-ROM drive, DVD drive, FLASH drive, RAM, ROM or any other electronic storage known in the art. The display can be implemented as an LCD display, CRT display, plasma display, OLED, LED or any other display known in the art. As such, the descriptions of the memory and the display provided herein are merely exemplary and in no way limit the scope of the present advancements.

While certain embodiments have been described, these embodiments have been presented by way of example only, and are not intended to limit the scope of the inventions. Indeed the novel methods and systems described herein may be embodied in a variety of other forms; furthermore, various omissions, substitutions, and changes in the form of the methods and systems described herein may be made without departing from the spirit of the inventions. The embodiments described herein are in no way restricted to a specific response function of the PCDs. Rather, the methods described in the above embodiments are applicable to any PCD that has its unique response function. The accompanying claims and their equivalents are intended to cover such forms or modifications as would fall within the scope and spirit of the inventions.

The invention claimed is:

1. A method for determining an optimal parameter vector, the parameter vector including a plurality of parameters of a detector response model of a photon-counting detector, the method comprising:
   determining a normalized measured photon count for each energy bin of the photon-counting detector;
   setting an initial incident photon spectrum and an initial value for each parameter of the plurality of parameters;
   calculating, using the detector response model, a normalized modeled photon count for each energy bin of the photon-counting detector, based on the incident photon spectrum and the plurality of parameters;
   computing, for each energy bin, a square of a difference between the normalized measured photon count and the normalized modeled photon count;
   weighting the computed square of each energy bin by a weighting factor to generate weighted squares;
   summing the weighted squares of each energy bin and computing a root-mean-square error for the photon-counting detector;
   updating at least one of the parameters of the parameter vector;
   repeating the calculating, computing, weighting, summing, and updating steps until a stopping criteria is met, so as to determine the optimal parameter vector;
   correcting measured count data obtained from a scan of a subject based on the deter mined optimal parameter vector to generate corrected count data; and
   reconstructing an image of a subject using the corrected count data.

2. The method of claim 1, wherein the determining step comprises:
   dividing a measured photon count of each energy bin by a total measured photon count of the photon-counting detector to determine the normalized photon count for each energy bin.

3. The method of claim 1, wherein the calculating step comprises:
   dividing a modeled photon count of each energy bin by a total modeled photon count of the photon-counting detector to calculate the normalized modeled photon count for each energy bin.

4. The method of claim 1, wherein the weighting step comprises weighting the computed square of each energy bin by the weighting factor for each energy bin of the photon counting detector, which is the normalized measured photon count of the energy bin.

5. The method of claim 1, wherein the step of computing the root-mean-square error (RMSE) of the photon counting detector comprises computing the RMSE as:

$$\text{RMSE} = \sqrt{\sum_{k=1}^{k=N} \varphi_k (\overline{C_k} - \overline{S_{out}(a)_k})^2},$$

wherein $\overline{C_k}$ is the normalized measured photon count of detector bin k, $\overline{S_{out}(a)_k}$ is the normalized modeled photon count of the detector bin k, $\phi_k$ is the weighting factor for detector bin k, and N is a number of detector bins in the photon counting detector.

6. The method of claim 1, wherein the optimal parameter vector is the parameter vector that yields a smallest value of the root-mean-square error.

7. The method of claim 1, wherein the updating step comprises updating the parameter vector according to an exhaustive search method.

8. The method of claim 1, wherein the updating step comprises updating the parameter vector according to one of Newton's method, a steepest descent method, a nonlinear conjugate gradient method, and a nonlinear least-squares method.

9. The method of claim 1, wherein the repeating step comprises repeating the calculating, computing, weighting, summing, and updating steps for a predetermined number of iterations.

10. A device for determining an optimal parameter vector, the parameter vector including a plurality of parameters of a detector response model of a photon-counting detector, the device comprising:
   a processing circuit configured to
      determine a normalized measured photon count for each energy bin of the photon-counting detector;
      set an initial incident photon spectrum and an initial value for each parameter of the plurality of parameters;
      calculate using the detector response model, a normalized modeled photon count for each energy bin of the photon-counting detector, based on the incident photon spectrum and the plurality of parameters;
      compute, for each energy bin, a square of a difference between the normalized measured photon count and the normalized modeled photon count;
      weight the computed square of each energy bin by a weighting factor to generate weighted squares;
      sum the weighted squares of each energy bin and compute a root-mean-square error for the photon-counting detector;

update at least one of the parameters of the parameter vector;

repeat the calculating, computing, weighting, summing, and updating steps until a stopping criteria is met, so as to determine the optimal parameter vector;

correct measured count data obtained from a scan of a subject based on the determined optimal parameter vector to generate corrected count data; and reconstruct an image of a subject using the corrected count data.

11. The device of claim 10, wherein the processing circuit is configured to determine the normalized measured photon count for each energy bin of the photon-counting by dividing a measured photon count of each energy bin by a total measured photon count of the photon-counting detector.

12. The device of claim 10, wherein the processing circuit is configured to weight the computed square of each energy bin by the weighting factor for each energy bin of the photon counting detector, which is the normalized measured photon count of the energy bin.

13. The device of claim 1, wherein processing circuit is configured to compute the root-mean-square error (RMSE) of the photon counting detector as:

$$\mathrm{RMS}E = \sqrt{\sum_{k=1}^{k=N} \varphi_k (\overline{C_k} - \overline{S_{out}(a)_k})^2},$$

wherein $\overline{C_k}$ is the normalized measured photon count of detector bin k, $\overline{S_{out}(a)_k}$ is the normalized modeled photon count of the detector bin k, $\phi_k$ is the weighting factor for detector bin k, and N is a number of detector bins in the photon counting detector.

14. The device of claim 10, wherein the optimal parameter vector is the parameter vector that yields a smallest value of the root-mean-square error.

15. The device of claim 10, wherein the processing circuit is further configured to update the parameter vector according to an exhaustive search method.

16. The device of claim 10, wherein the processing circuit is further configured to update the parameter vector according to one of Newton's method, a steepest descent method, a nonlinear conjugate gradient method, and a nonlinear least-squares method.

17. The device of claim 10, wherein the processing circuit is further configured to repeat the calculating, computing, weighting, summing, and updating steps for a predetermined number of iterations.

18. A non-transitory computer-readable medium having stored thereon a program that when executed by a computer causes the computer to execute a method comprising:

determining a normalized measured photon count for each energy bin of the photon-counting detector;

setting an initial incident photon spectrum and an initial value for each parameter of the plurality of parameters;

calculating, using the detector response model, a normalized modeled photon count for each energy bin of the photon-counting detector, based on the incident photon spectrum and the plurality of parameters;

computing, for each energy bin, a square of a difference between the normalized measured photon count and the normalized modeled photon count;

weighting the computed square of each energy bin by a weighting factor to generate weighted squares;

summing the weighted squares of each energy bin and computing a root-mean-square error for the photon-counting detector;

updating at least one of the parameters of the parameter vector;

repeating the calculating, computing, weighting, summing, and updating steps until a stopping criteria is met, so as to determine the optimal parameter vector;

correcting measured count data obtained from a scan of a subject based on the determined optimal parameter vector to generate corrected count data; and reconstructing an image of a subject using the corrected count data.

19. The non-transitory computer readable medium of claim 18, wherein the step of computing the root-mean-square error (RMSE) of the photon-counting detector comprises computing RMSE as:

$$\mathrm{RMS}E = \sqrt{\sum_{k=1}^{k=N} \varphi_k (\overline{C_k} - \overline{S_{out}(a)_k})^2},$$

wherein $\overline{C_k}$ is the normalized measured photon count of detector bin k, $\overline{S_{out}(a)_k}$ is the normalized modeled photon count of the detector bin k, $\phi_k$ is the weighting factor for detector bin k, and N is a number of detector bins in the photon counting detector.

20. The non-transitory computer readable medium of claim 18, wherein the weighting step comprises weighting the computed square of each energy bin by the weighting factor for each energy bin of the photon counting detector, which is the normalized measured photon count of the energy bin.

* * * * *